(12) United States Patent
Straessler et al.

(10) Patent No.: US 8,658,818 B2
(45) Date of Patent: Feb. 25, 2014

(54) METHODS OF PRODUCING NITRATE ESTERS

(75) Inventors: Nicholas A. Straessler, North Salt Lake, UT (US); Alexander J. Paraskos, Ogden, UT (US); Michael P. Kramer, Wellsville, UT (US)

(73) Assignee: Alliant Techsystems Inc., Arlington, VA (US)

( * ) Notice: Subject to any disclaimer, the term of this patent is extended or adjusted under 35 U.S.C. 154(b) by 116 days.

(21) Appl. No.: 12/953,111

(22) Filed: Nov. 23, 2010

(65) Prior Publication Data

US 2012/0130115 A1    May 24, 2012

(51) Int. Cl.
*C07C 203/04* (2006.01)

(52) U.S. Cl.
USPC ............ 558/483; 558/484; 558/485; 558/486

(58) Field of Classification Search
None
See application file for complete search history.

(56) References Cited

U.S. PATENT DOCUMENTS

| | | | |
|---|---|---|---|
| 4,014,720 A | 3/1977 | Wells | |
| 5,454,891 A | 10/1995 | Preston | |
| 5,529,649 A | 6/1996 | Lund et al. | |
| 7,737,308 B1 * | 6/2010 | Straessler | 568/706 |
| 2003/0089435 A1 * | 5/2003 | Sanderson et al. | 149/19.1 |
| 2007/0287852 A1 * | 12/2007 | Antes et al. | 558/480 |

FOREIGN PATENT DOCUMENTS

| | | |
|---|---|---|
| IN | 189917 A1 | 5/2003 |
| IN | 189917 A1 * | 5/2003 |

OTHER PUBLICATIONS

Bellamy, Journal of Hazardous Marerials 59(2-3)(1998):145-157.*
Agrawal, J.P., et al., Synthetic Routes to Nitrate Esters, Organic Chemistry of Explosives, Chapter 3, 2007, pp. 87-91, John Wiley & Sons, Ltd.
Meyer, Rudolf, et al., Explosives, Fifth Completely Revised Edition, 2002, pp. 48, 49, 98, 99, 226-228, 253, 254, 346, and 347, Wiley-VCH Verlag GMBH.
Urbanski, Tadeusz, Nitration with Nitrating Mixtures, Chemistry and Technology of Explosives, vol. 1, Chapter IV, 1964, pp. 139-164, Pergamon Press.
United States Boosters and Secondary Explosives, Military Explosives, Department of the Army Technical Manual TM 9-1300-214, Chapter 8, Sep. 1984, pp. 8-1, 8-2, 8-9 through 8-14, and 8-16 through 8-27.

* cited by examiner

*Primary Examiner* — Nyeemah A Grazier
(74) *Attorney, Agent, or Firm* — TraskBritt

(57) ABSTRACT

Methods of forming a nitrate ester include combining at least one nitrate salt and sulfuric acid to form a nitrating solution and adding an aliphatic polyol to the nitrating solution. Nitrate esters formed by this method may be, for example, triethylene glycol dinitrate (TEGDN), pentaerythritol tetranitrate (PETN), diglycerol tetranitrate (DGTN), 1,1,1-tris(methylol)ethane trinitrate (TMETN), 1,2,4-butanetriol trinitrate (BTTN), nitroglycerin (NG), diethylene glycol dinitrate (DEGDN), ethylene glycol dinitrate (EGDN), metriol trinitrate (MTN), nitrocellulose (NC), or 1,2-propanediol dinitrate (PDDN).

20 Claims, 6 Drawing Sheets

METHODS OF PRODUCING NITRATE ESTERS

TECHNICAL FIELD

Embodiments of the present disclosure relate to nitrate ester synthesis and, more specifically, to methods of producing nitrate esters using ammonium nitrate and sulfuric acid.

BACKGROUND

Nitrate-ester plasticizers are commonly used in commercial and military explosives and propellants. For example, glyceryl trinitrate (nitroglycerine, or simply NG) is used in dynamite and in double-base propellants, and triethylene glycol dinitrate (TEGDN) is used in tactical propellant systems. Nitrate esters are conventionally produced by a nitration reaction of a polyol with a so-called "mixed acid," which includes nitric acid ($HNO_3$) and sulfuric acid ($H_2SO_4$). See, e.g., J. P. Agrawal and R. D. Hodgson, Organic Chemistry of Explosives, pp. 90 and 91 (2007). The mixed acid contains nitrating species, such as nitronium ions ($—NO_2^+$) which react with hydroxyl groups on a polyol starting material, substituting a nitro group for the hydrogen in an O-nitration reaction. The mixed acid nitration reaction is used to synthesize NG from the polyol glycerin (glycerol) and TEGDN from the polyol triethylene glycol (TEG). These mixed acid nitration reactions may be performed in a Biazzi nitrator or other continuous-type configuration, such as a pipe nitrator. Mixed acid nitration reactions and reaction equipment are described in Military Explosives, Dept. of the Army Technical Manual, TM No. 9-1300-214, pp. 8-10 to 8-13 (1984). The mixed acid nitration reaction utilizes an extended washing train system to extract the nitrate ester. Nitration may also be conducted utilizing only nitric acid, which is referred to herein as a nitric acid nitration reaction.

Other nitrate esters may be formed by similar mechanisms. For example, ethylene glycol dinitrate (EGDN or nitroglycol), diethylene glycol dinitrate (DEGDN), diglycerol tetranitrate (DGTN), metriol trinitrate (MTN), 1,2,4-butanetriol trinitrate (BTTN), 1,2-propanediol dinitrate (PDDN), trimethylolethane trinitrate (TMETN), and pentaerythritol tetranitrate (PETN) may be formed by the mixed acid nitration reaction of ethylene glycol, diethylene glycol, diglycerol, methyltrimethylolmethane (metriol), 1,2,4-butanetriol (BT), 1,2-propanediol, 1,1,1-tris(hydroxymethyl)-ethane (THME), and pentaerythritol, respectively.

However, mixed acid nitration reactions have a number of disadvantages. Because the nitration reactions are exothermic, special care must be, and is, taken to avoid thermal runaway and explosions, especially in large-scale processes. In addition, the high solubility and thermal instability of the nitrate esters in the mixed acid lead to poor separation of the nitrate ester. Furthermore, dissolved nitrate esters in the waste acid may react with nitric acid, resulting in violent oxidative fume-off. An extended water washing train may be used to limit these problems. However, additional processing equipment may be required to safely remove or destroy the nitrate ester residue present in the waste water streams.

Furthermore, oxidative side reactions and fume-off of nitric acid may reduce the concentration of the active nitrating agent in mixed acid nitrations. Therefore, excess nitric acid may be required for such reactions. In the case of nitric acid nitration reactions, the molar ratio of $HNO_3$ to $—OH$ is essentially infinite since the nitric acid also serves as the solvent.

Because of the difficulty and expense of processing excess reagents and large volumes of hazardous waste streams, some nitrate esters are not in production domestically. For example, the Naval Surface Warfare Center, Indian Head Division, and Copperhead Chemical have both stopped current production of TEGDN. The complexity of the required equipment makes production of some nitrate esters economically unattractive, leading to sporadic commercial availability of these compounds.

Other methods of nitrating compounds are also known. Carbon atoms of some aromatic compounds may be nitrated using a mixture of a nitrate salt and sulfuric acid, as described in U.S. Pat. No. 7,737,308, which is assigned to the Assignee of the present application. A polycyclic nitramine, such as 4,10-dinitro-2,6,8,12-tetraoxa-4,10-diazatetracyclo [$5.5.0.0^{5,9}0^{3,11}$] dodecane (TEX), may be formed by nitration of nitrogen atoms on a cyclic hydrocarbon using ammonium nitrate as a nitrate source, as described in U.S. Pat. No. 5,529,649, which is assigned to the Assignee of the present application.

BRIEF SUMMARY

One embodiment of the present disclosure includes a method of producing a nitrate ester. The method comprises combining at least one nitrate salt and sulfuric acid to form a nitrating solution. An aliphatic polyol is added to the nitrating solution.

Another embodiment of the present disclosure includes a method of producing a nitrate ester that comprises reacting an aliphatic polyol with a nitrating solution comprising sulfuric acid and at least one nitrate salt.

BRIEF DESCRIPTION OF THE DRAWINGS

While the specification concludes with claims particularly pointing out and distinctly claiming that which is regarded as the invention, advantages of this invention may be more readily ascertained from the following detailed description when read in conjunction with the accompanying drawing in which:

DETAILED DESCRIPTION

Figure 1:
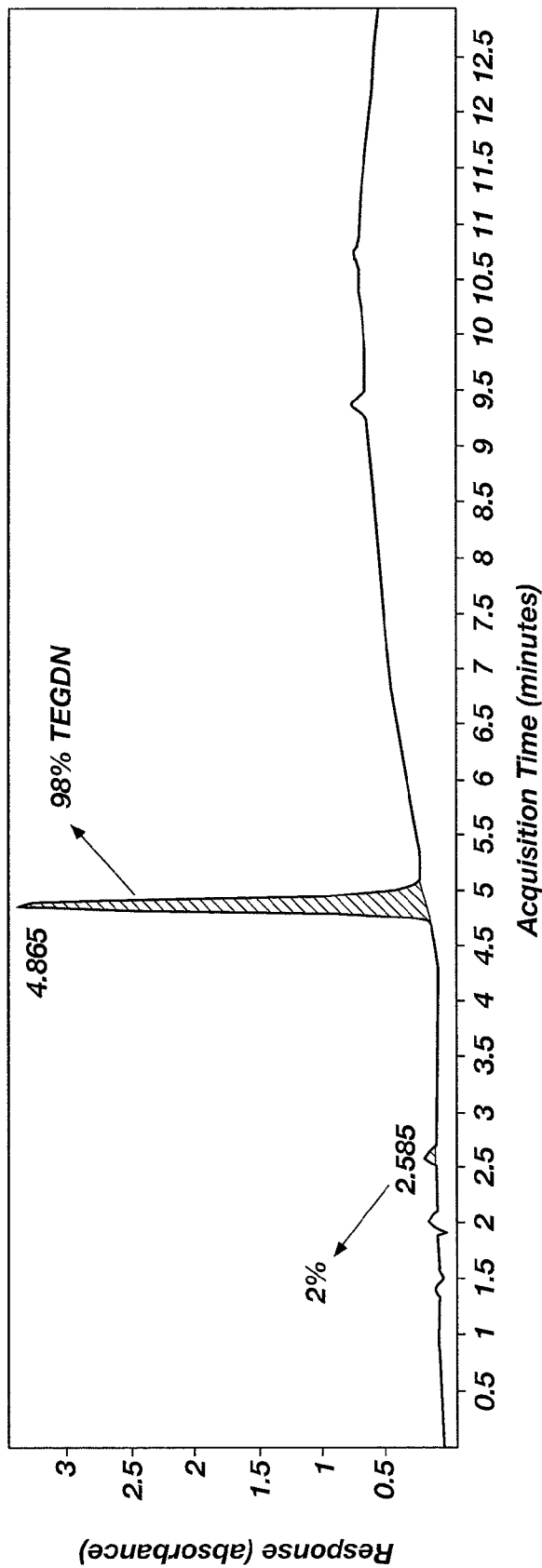
FIGS. 1 through 6 comprise HPLC/UV chromatograms showing the purity of nitrate esters formed according to embodiments of the present disclosure.

Methods of producing a nitrate ester are described. The methods utilize a nitrating solution that includes a nitrate salt and sulfuric acid as a nitrating source. Nitric acid is formed in situ by the reaction of the nitrate salt with the sulfuric acid. By reacting an aliphatic polyol with nitronium ions in the nitrating solution, at least one nitro functional group ($—NO_2$) may be added to oxygen atoms of hydroxyl groups of the aliphatic polyol, producing the nitrate ester. By utilizing the nitrating solution, the nitrate ester may be produced under milder (i.e., less oxidizing) conditions than the mixed acid nitration reaction, which reduces safety concerns and costs associated with disposal of hazardous waste streams.

To form the nitrate ester, the aliphatic polyol and the nitrating solution may be combined in a reaction vessel to produce a reaction mixture. As previously described, the nitrating solution may include the nitrate salt and sulfuric acid. The aliphatic polyol may be directly nitrated by nitronium ions in the nitrating solution. The term "directly nitrated" means and includes nitrating the aliphatic polyol in a single reaction act, without forming an intermediate compound that is subsequently nitrated. The aliphatic polyol may be a starting material for the nitrate ester. Depending on the nitrate ester to be formed, the aliphatic polyol may be TEG, pentaerythritol, diglycerol, 1,1,1-tris(hydroxymethyl)-ethane (THME), 1,2,4-butanetriol (BT), glycerin, diethylene glycol, ethylene glycol, metriol, cellulose, or 1,2-propanediol. The aliphatic polyol may be a solid (e.g., pentaerythritol or THME) or a liquid (e.g., TEG, diglycerol, or glycerin) at room temperature.

The nitrate salt may be sodium nitrate ($NaNO_3$), potassium nitrate ($KNO_3$), ammonium nitrate ($NH_4NO_3$), calcium nitrate ($Ca(NO_3)_2$), magnesium nitrate ($Mg(NO_3)_2$), another metal nitrate, or a combination thereof. In one embodiment, the nitrate salt is ammonium nitrate. The nitrate salt may be commercially available from various sources, such as from Sigma-Aldrich Co. (St. Louis, Mo.) or from Acros Organics (Morris Plains, N.J.). The sulfuric acid may be concentrated sulfuric acid (from about 95% to about 98% sulfuric acid), which is commercially available from various sources, such as from Sigma-Aldrich Co. (St. Louis, Mo.). However, a lower concentration of sulfuric acid may also be used, wherein sulfuric acid is purchased commercially at a lower concentration, or wherein concentrated sulfuric acid is diluted, such as with water. The diluted sulfuric acid may include a sufficient concentration of sulfuric acid to form nitronium ions, as described below. The diluted sulfuric acid may include a sulfuric acid concentration of greater than or equal to about 50% by weight (wt %). For instance, in some embodiments, the sulfuric acid solution may include from about 70 wt % to about 95 wt % sulfuric acid, such as about 80 wt % sulfuric acid, with water accounting for the remainder of the solution. The term "sulfuric acid" is used herein to refer to a concentrated sulfuric acid or a solution of concentrated sulfuric acid diluted with water. Without being bound by a particular theory, water, if present in the nitrating solution, may improve the yield of the nitrate ester. For example, the aliphatic polyol may be a viscous liquid that is more soluble in water than in concentrated sulfuric acid. Likewise, the nitrate salt may be more soluble in water than in concentrated sulfuric acid. By diluting the sulfuric acid with water, the solubility of the aliphatic polyol and the nitrate salt in the reaction mixture may be increased, which increases the rate of the nitration reaction and enables shorter reaction times.

The nitrating solution may be produced by combining the nitrate salt and the sulfuric acid. The sulfuric acid may be cooled, such as to a temperature of about 5° C., before adding the nitrate salt. The temperature of the sulfuric acid may be reduced using a cooling source, such as an ice bath or a cooling or heat exchange system. For safety reasons, the sulfuric acid may be maintained at a temperature below about 20° C., such as below about 15° C., as the nitrate salt is added. However, the nitrating solution may be maintained at a higher temperature if an increased reaction rate is desired. Nitric acid is formed in situ by the reaction of the nitrate salt and the sulfuric acid. At any given time, the nitrating solution may include the nitrate salt, sulfuric acid, nitric acid, nitronium ions ($-NO_2^+$), and $H_2O$. The nitrating solution may be milder than a mixed acid system (a mixture of sulfuric acid and nitric acids) due to the additional equilibrium that produces the nitronium ion:

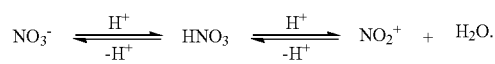

This equilibrium enables better control over the active nitrating species and suppresses the amount of oxidizing species present at any given time in solution.

The aliphatic polyol may be added to the nitrating solution, with stirring, to form the reaction mixture. The aliphatic polyol may be added to the nitrating solution stepwise, continuously, or in a single portion. The nitration reaction may be conducted in a conventional reaction vessel, such as a round-bottom flask or a reactor. The reaction vessel may be compatible with the conditions of the nitration reaction. By way of example, when commercial quantities of the nitrate ester are to be produced, the reaction vessel may be a 5-, 50-, or 500-gallon Pfaudler type glass-lined reactor. During the addition of the aliphatic polyol, the nitrating solution may be cooled (e.g., with an ice bath or a cooling or heat exchange system) because the addition of the aliphatic polyol may be exothermic. Once the temperature of the reaction mixture starts to decrease, the cooling source may be removed or operation thereof stopped. During the nitration reaction, the temperature of the reaction mixture may be maintained between about 0° C. and about 80° C., such as from about 10° C. to about 70° C. or from about 20° C. to about 50° C. For safety reasons, the reaction mixture may initially be maintained at a temperature of less than or equal to about 15° C. and then warmed to room (ambient) temperature (from about 20° C. to about 25° C.). However, the reaction mixture may be maintained at a higher temperature if an increased reaction rate is desired, so long as the nitrate ester does not degrade. Unlike mixed acid nitration reactions, the reaction mixture of the method of the present disclosure may be heated without fuming off nitric acid or other observable oxidized nitrogen species (e.g., $NO_x$). Since a higher temperature corresponds to a higher reaction rate, the reaction time of the method of the present disclosure may be decreased by heating the reaction vessel or by removing the cooling source, such as the ice bath.

The nitronium ions in the nitrating solution may react with the aliphatic polyol, forming the nitrate ester, ammonium sulfate, and excess sulfuric acid. Depending on the aliphatic polyol used, the nitrate ester produced may be TEGDN, PETN, DGTN, TMETN, BTTN, NG, DEGDN, EGDN, MTN, nitrocellulose (NC), or PDDN. The reaction mixture may include from about 1.0 molar equivalent to about 2.0 molar equivalents of the nitrate salt for each hydroxyl group on the aliphatic polyol. By way of example, 1.0 molar equivalent of the nitrate salt, 1.1 molar equivalents of the nitrate salt, 1.2 molar equivalents of the nitrate salt, 1.5 molar equivalents of the nitrate salt, or 2.0 molar equivalents of the nitrate salt may be used. While equimolar amounts of the nitrate salt relative to the number of hydroxyl groups on the aliphatic polyol may be used, to ensure complete nitration of the aliphatic polyol, the reaction mixture may include about two or more molar equivalents of the nitrate salt for each hydroxyl group on the aliphatic polyol. By way of example, if TEGDN is to be produced from TEG, four molar equivalents of the nitrate salt may be used per molar equivalent of TEG since TEG has two hydroxyl groups. Using greater than two molar equivalents of the nitrate salt for each hydroxyl group on the aliphatic polyol may enable the nitration reaction to be conducted at an increased reaction rate or produce an increased yield of the nitrate ester. By using the nitrate salt as the nitrating source, instead of nitric acid (as in the mixed acid nitration reaction), a lower molar ratio of nitronium ions may be utilized for complete reaction with the aliphatic polyol. In contrast, in mixed acid nitration reactions or nitric acid nitration reactions, about 2.2 moles of nitric acid or more per hydroxyl group on the polyol are used to ensure completion of the nitration reaction.

The aliphatic polyol may be reacted with the nitrating solution for an amount of time sufficient for the nitrate ester to form. By way of example, the reaction time may range from about 10 minutes to about 4 hours. However, the reaction time may be longer or shorter depending on the reaction conditions. Furthermore, while the nitration reaction is described herein as being conducted in a batch process, the nitration reaction may be conducted in a continuous flow process, in which case the reaction time may vary depending on factors such as reactor volume and flow rate. The continuous flow process may be conducted in a Biazzi reactor or other suitable reactor configured for a continuous flow process.

Utilizing the nitrate salt as the nitrating source may limit the amount of nitric acid present in the nitrating solution at any one time, which in turn, is believed to limit undesirable oxidative side reactions of the aliphatic polyol or of intermediate reaction products. Excess nitric acid is believed to be responsible for the oxidative "fume off" behavior of waste streams in the mixed acid nitration reaction. Reducing the concentration of excess nitric acid in the method of the present disclosure may reduce or eliminate safety and disposal concerns with the nitric acid. In addition, utilizing the nitrating solution of the present disclosure may reduce or eliminate the handling of nitric acid, which is highly corrosive and toxic. The nitrate salt of the nitrating solution is less hazardous than nitric acid and, therefore, may be easier to store and use. Because the nitrating solution is milder than the mixed acid system, the nitration reaction may be conducted in a conventional reaction vessel, rather than utilizing the Biazzi nitrator and the washing train system of the mixed acid nitration reaction. Therefore, the method of producing the nitrate ester according to the present disclosure may be less complex than the mixed acid nitration reaction.

The reduced nitric acid concentration in the nitrating solution may also minimize the amount of nitrate ester remaining in a waste stream of the nitration reaction because the nitrate ester is less soluble in the reaction mixture than in the mixed acid system of a mixed acid nitration reaction. Since degradation and oxidation of the nitrate ester may occur when the nitrate ester is exposed to a high concentration of nitric acid, the method of the present disclosure may avoid such negative effects due to the lower solubility of the nitrate ester in the reaction mixture. Furthermore, a higher yield of the nitrate ester may be achieved because of a lower rate of oxidation of the nitrate ester. The lower nitric acid concentration in the reaction mixture may also limit or minimize the amount of hazardous products, such as oxidized nitrogen species ($NO_x$), formed during nitration of the aliphatic polyol and separation of the nitrate ester.

After formation of the nitrate ester, the reaction mixture may be quenched so that the nitrate ester may be recovered. By way of example, the nitration reaction may be quenched by adding ice to the reaction mixture, which decreases the sulfuric acid concentration and the temperature of the reaction mixture. In addition to the nitrate ester, intermediate reaction products in which the aliphatic polyol is not completely nitrated (e.g., under-nitrated intermediate reaction products) may be present in the reaction mixture. The identity and concentration of such intermediate reaction products may vary based on the reaction conditions preceding the quenching. Such intermediate reaction products may be separated from the nitrate ester products and recycled (e.g., into another batch reaction mixture, or back into a feed stream of a continuous flow reaction). The concentration of such intermediate reaction products may be minimized by selecting appropriate operating conditions.

Since the nitrate ester produced by the nitration reaction is relatively insoluble in water, an emulsion of the nitrate ester in the reaction mixture may be formed. The nitrate ester may be isolated from the reaction mixture, such as by using conventional filtration techniques or conventional liquid-liquid separation or extraction techniques, which are not described in detail herein. The separation technique may be determined by a person of ordinary skill in the art depending on whether the nitrate ester is a solid or a liquid. If the nitrate ester is a solid, such as PETN, the nitrate ester may be isolated from the reaction mixture by filtration and washed with water and/or an aqueous base (e.g., sodium bicarbonate). If the nitrate ester is a liquid, such as TEGDN, the nitrate ester may be extracted with an organic solvent, dried, and concentrated. The organic solvent may be methylene chloride, ethyl acetate, butyl acetate, chloroform, or another water immiscible liquid in which the nitrate ester is soluble.

After separation, the nitrate ester may be washed, dried, and concentrated to remove byproducts (e.g., under-nitrated intermediate reaction products) or contaminants of the nitration reaction. The yield of the resulting nitrate ester may be greater than about 50%, such as greater than about 60%, greater than about 70%, greater than about 80%, or greater than about 90%. The nitrate ester may be substantially pure, such as greater than 90% purity. If, however, a higher purity is desired, the nitrate ester may be subjected to additional purification, such as chromatography, recrystallization, or filtration. Because of the lower amounts of byproducts formed and the lower solubility of the nitrate ester in the reaction mixture, the number of washing acts to separate the nitrate ester from the reaction mixture may be reduced. This may lead to a decrease in the generation of liquid waste that contains the nitrate ester, an energetic material, and, thus, disposal costs and overall operating costs for the production of the nitrate ester may be reduced.

The nitrate ester may be utilized as a plasticizer in a propellant, explosive, or other energetic composition. Such compositions are known in the art and, therefore, other components of such compositions are not described in detail herein. The nitrate ester may have sufficient purity to minimize degradation of other components in a composition since impurities from the nitration reaction may be incompatible with the other components. For example, in military applications in which compositions that include the nitrate ester are manufactured years in advance of when they will be used, long-term stability may be important. This may be especially true for propellants or explosives stored near personnel (e.g., on vessels at sea) or in extreme conditions (e.g., in desert magazines). In such cases, users of the compositions may demand not only high purity, but characterization of the impurities in the composition, such as those in the nitrate ester. Utilizing appropriate separation techniques to recover the nitrate ester may reduce or eliminate problems associated with impurities in finished propellants and explosives, including necessary characterization of impurities before use, degradation of impurities, and reactions of impurities with other components of the compositions.

The following examples serve to explain embodiments of the method of forming nitrate esters in more detail. These examples are not to be construed as being exhaustive or exclusive as to the scope of the invention.

EXAMPLES

The polyol precursors were purchased from commercial sources, such as Sigma-Aldrich Co. (St. Louis, Mo.) or Solvay Solexis, Inc. (West Deptford, N.J.). Ammonium nitrate (≥98% purity) was purchased from Sigma-Aldrich Co.

(St. Louis, Mo.). Sulfuric acid (95%-98% concentration) was purchased from Acros Organics (Morris Plains, N.J.).

Example 1

Nitration of Triethylene Glycol (TEG) to Form Triethylene Glycol Dinitrate (TEGDN)

A round-bottom flask was charged with a magnetic stir bar and 10 mL of sulfuric acid, and then chilled in an ice bath. Ammonium nitrate (4.8 g (60 mmol)) was added at a rate such that the temperature of the nitrating solution did not exceed 20° C. TEG (2 mL (15 mmol), 99% purity, purchased from Sigma-Aldrich Co.) was added at a rate such that the temperature of the reaction mixture did not exceed 20° C. Once all the TEG was added and the temperature of the reaction mixture began to decrease, the ice bath was removed and the reaction mixture was stirred for 2 hours at ambient conditions. The reaction mixture was added in one portion to 50 g crushed ice and stirred gently until all the ice melted. The resulting emulsion was transferred to a separatory funnel and extracted three times with 20 mL methylene chloride. The combined organic extracts were dried with MgSO$_4$ and then concentrated to produce TEGDN as a clear colorless liquid (2.27 g of TEGDN, a 63% yield). The reaction is shown below:

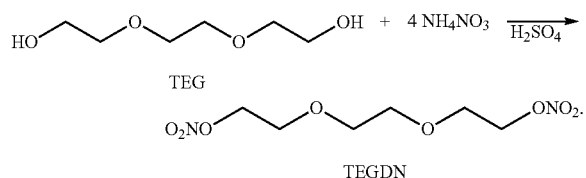

The TEGDN was characterized by proton and carbon nuclear magnetic resonance ($^1$H NMR, $^{13}$C NMR) spectroscopy and high performance liquid chromatography (HPLC). These analyses were conducted according to conventional techniques and, therefore, are not described in detail herein. As shown in FIG. 1, the TEGDN was about 98% pure. The $^1$H and $^{13}$C NMR spectra (not shown) confirmed the synthesis of TEGDN.

Example 2

Nitration of Pentaerythritol to Form Pentaerythritol Tetranitrate (PETN)

A round-bottom flask was charged with a magnetic stir bar and 10 mL of sulfuric acid, and then chilled in an ice bath. Ammonium nitrate (2.36 g (29.4 mmol)) was added at a rate such that the temperature of the nitrating solution did not exceed 15° C. Pentaerythritol (0.5 g (3.7 mmol), ≥99% purity, purchased from Sigma-Aldrich Co.) was added in a single portion, with no notable exotherm. The ice bath was removed and the reaction mixture was stirred for 2 hours at ambient conditions. The reaction mixture was added in one portion to 50 g crushed ice and stirred gently until all the ice melted. The resulting precipitate was separated by filtration, rinsed with cold water, and air dried to produce PETN as a white solid (0.72 g of PETN, a 62% yield). The reaction is shown below:

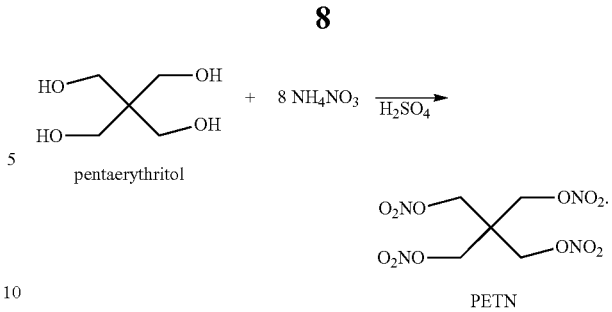

Figure 2:
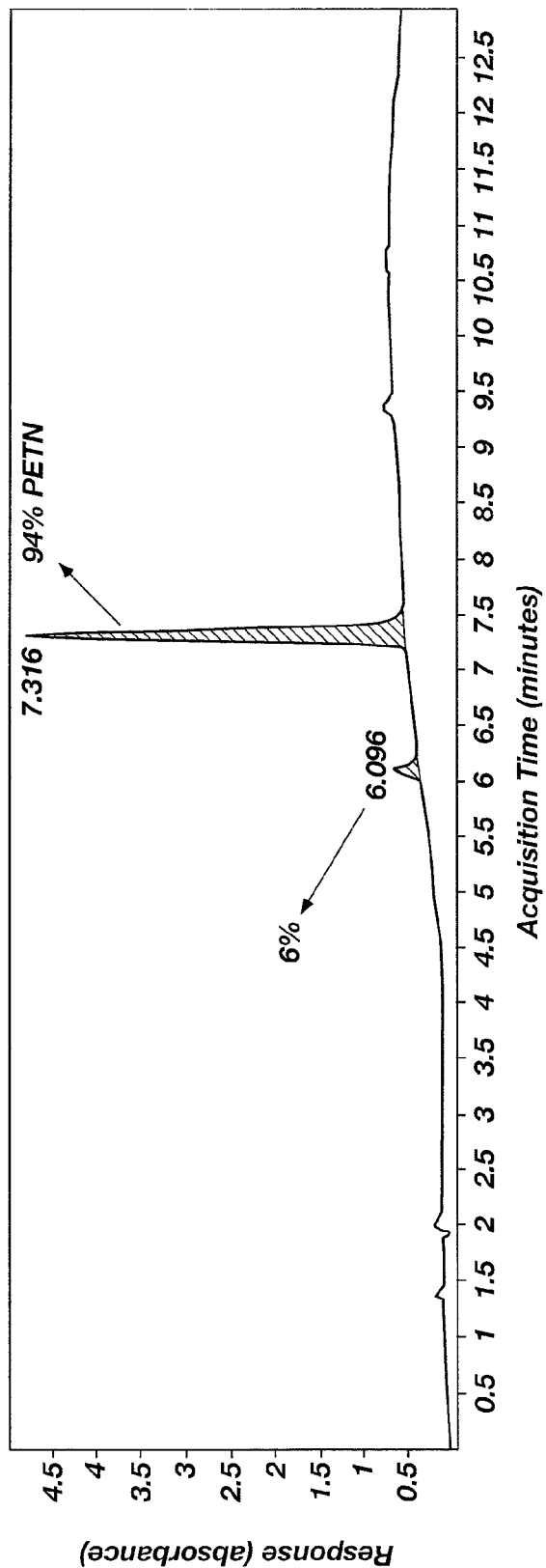

The PETN was characterized by $^1$H and $^{13}$C NMR spectroscopy and HPLC. As shown in FIG. 2, the PETN was about 94% pure. The $^1$H and $^{13}$C NMR spectra (not shown) confirmed the synthesis of PETN

Example 3

Nitration of Diglycerol to Form Diglycerol Tetranitrate (DGTN)

A round-bottom flask was charged with a magnetic stir bar and 10 mL of sulfuric acid, and then chilled in an ice bath. Ammonium nitrate (3.85 g (48.1 mmol)) was added at a rate such that the temperature of the nitrating solution did not exceed 15° C. Diglycerol (1.0 g (6.01 mmol), >90% purity, purchased from Solvay Solexis, Inc.) was added at a rate such that the temperature of the reaction mixture did not exceed 15° C. Once all the diglycerol was added and the temperature of the reaction mixture began to decrease, the ice bath was removed and the reaction mixture was stirred for 1.5 hours at ambient conditions. The reaction mixture was added in one portion to 50 g crushed ice and stirred gently until all the ice melted. The resulting emulsion was transferred to a separatory funnel and extracted three times with 25 mL methylene chloride. The combined organic extracts were dried with MgSO$_4$ and then concentrated to produce DGTN as a clear pale yellow liquid (1.17 g of DGTN, a 56% yield). The reaction is shown below:

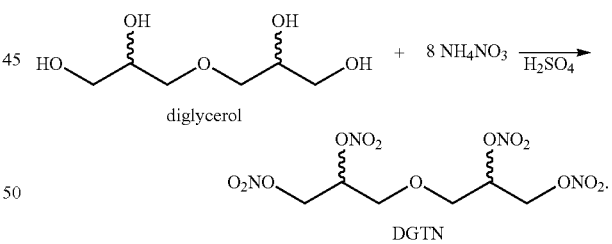

Figure 3:
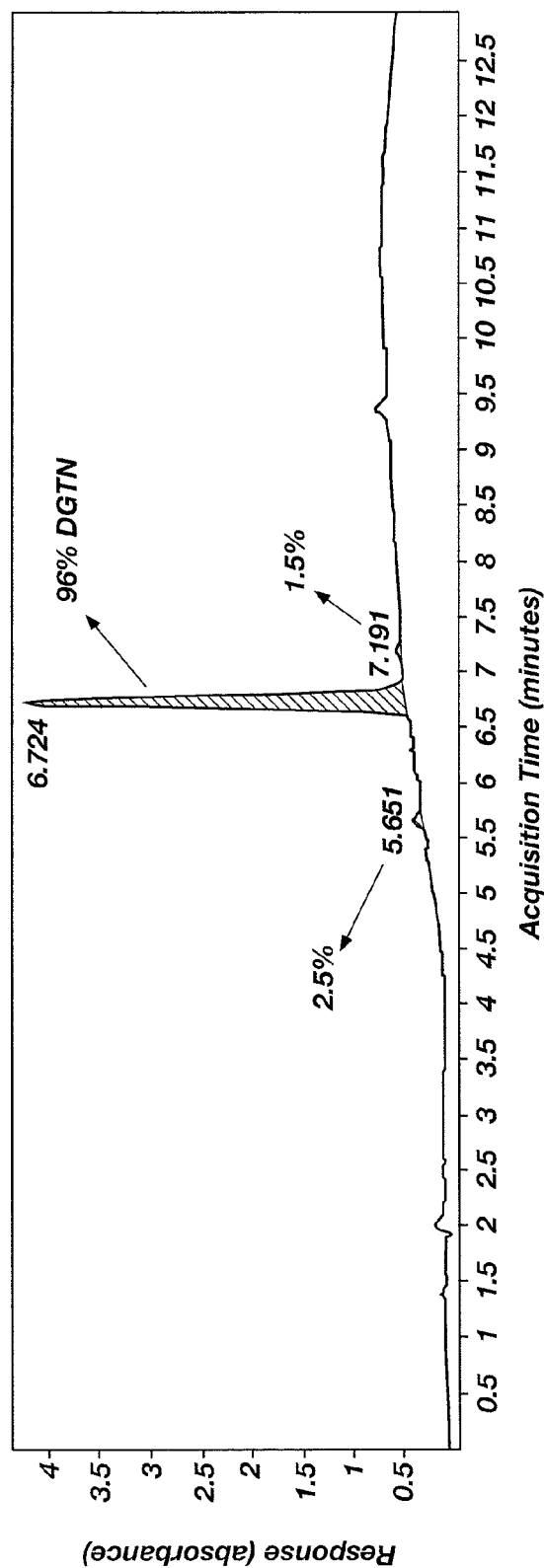

The DGTN was characterized by $^1$H and $^{13}$C NMR spectroscopy and HPLC. As shown in FIG. 3, the DGTN was about 96% pure. The $^1$H and $^{13}$C NMR spectra (not shown) confirmed the synthesis of DGTN.

Example 4

Nitration of 1,1,1-Tris(hydroxymethyl)-ethane (THME) to Form 1,1,1-Tris(methylol)ethane trinitrate (TMETN)

A round-bottom flask was charged with a magnetic stir bar and 10 mL of sulfuric acid, and then chilled in an ice bath. Ammonium nitrate (2.0 g (25 mmol)) was added at a rate such that the temperature of the nitrating solution did not exceed 15° C. THME (0.5 g (4.16 mmol), 99% purity, purchased from Sigma-Aldrich Co.) was added in a single portion. The reaction mixture was stirred at a temperature from about 0° C. to about 5° C. for 4 hours. The reaction mixture was added in one portion to 50 g crushed ice and stirred gently until all the ice melted. The resulting emulsion was transferred to a separatory funnel and extracted three times with 25 mL methylene chloride. The combined organic extracts were dried with $MgSO_4$ and then concentrated to produce TMETN as a clear colorless liquid (0.54 g of TMETN, a 51% yield). The reaction is shown below:

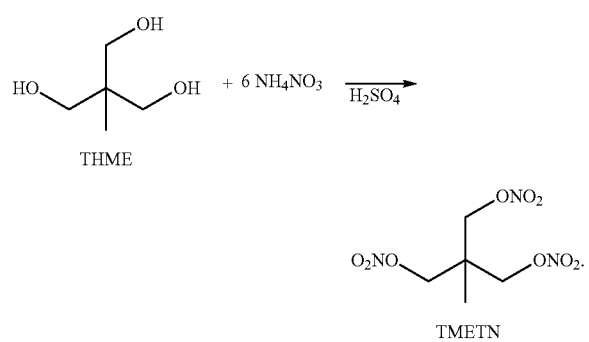

Figure 4:
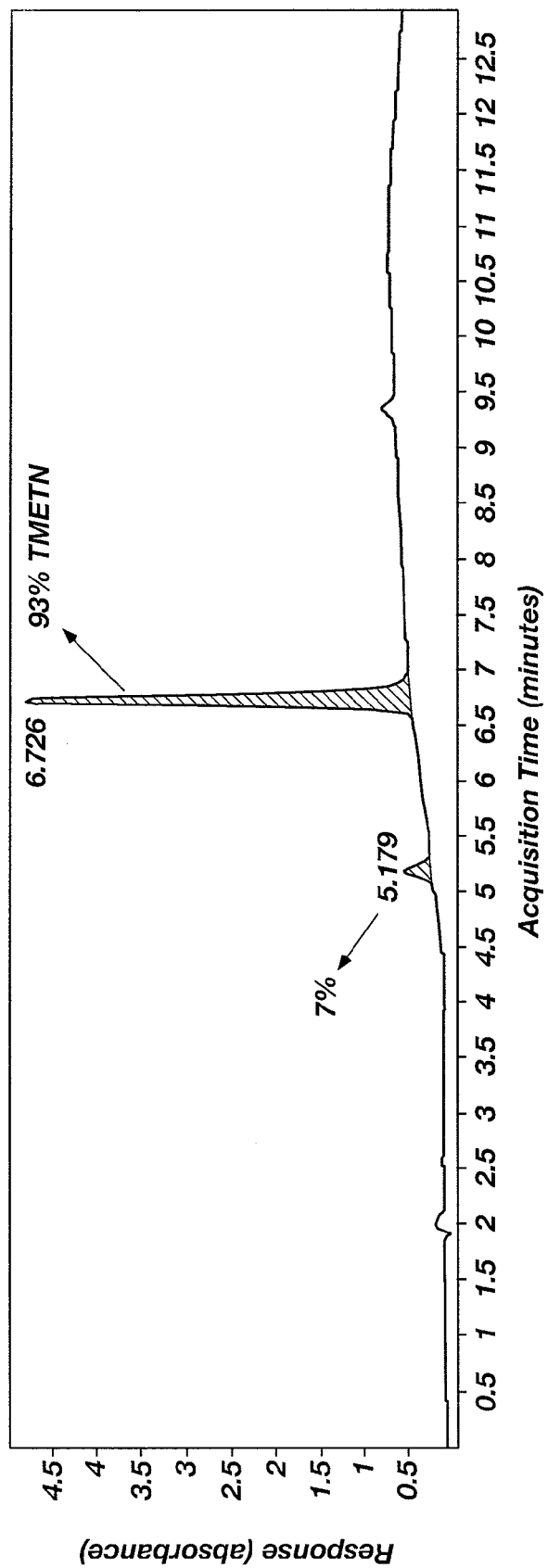

The TMETN was characterized by $^1H$ and $^{13}C$ NMR spectroscopy and HPLC. As shown in FIG. 4, the TMETN was about 93% pure. The $^1H$ and $^{13}C$ NMR spectra (not shown) confirmed the synthesis of TMETN.

Example 5

Nitration of 1,2,4-Butanetriol (BT) to Form 1,2,4-Butanetriol Trinitrate (BTTN)

A round-bottom flask was charged with a magnetic stir bar and 25 mL of sulfuric acid, and then chilled in an ice bath. Ammonium nitrate (10.76 g (134.4 mmol)) was added at a rate such that the temperature of the nitrating solution did not exceed 15° C. BT (2 mL (22.4 mmol), 95% purity, purchased from Sigma-Aldrich Co.) was added at a rate such that the temperature of the reaction mixture did not exceed 15° C. Once all the BT was added and the temperature of the reaction mixture began to decrease, the ice bath was removed and the reaction was stirred for 3 hours at ambient conditions. The reaction mixture was added in one portion to 100 g crushed ice and stirred gently until all the ice melted. The resulting emulsion was transferred to a separatory funnel and extracted four times with 25 mL methylene chloride. The combined organic extracts were dried with $MgSO_4$ and then concentrated to produce BTTN as a clear pale yellow liquid (4.3 g of BTTN, an 80% yield). The reaction is shown below:

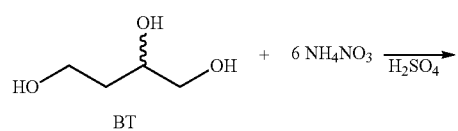

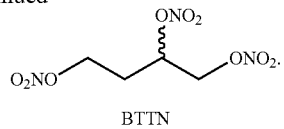

Figure 5:
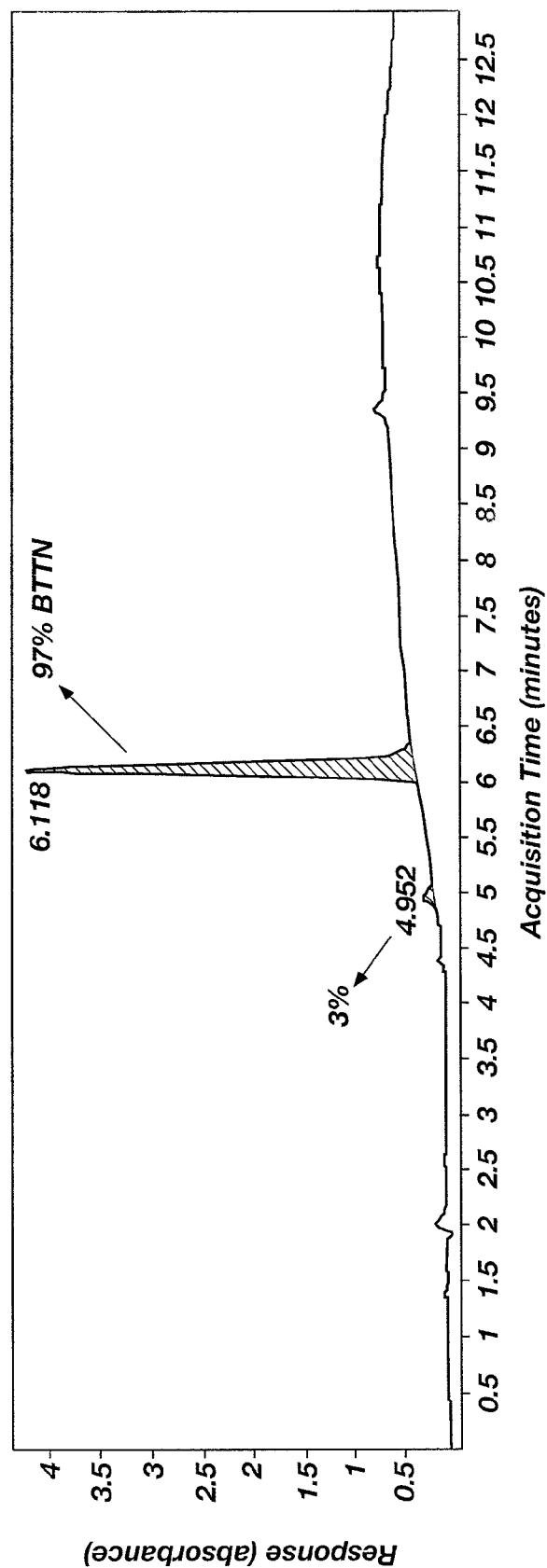

The BTTN was characterized by $^1H$ and $^{13}C$ NMR spectroscopy and HPLC. As shown in FIG. 5, the BTTN was about 97% pure. The $^1H$ and $^{13}C$ NMR spectra (not shown) confirmed the synthesis of BTTN.

Example 6

Nitration of Glycerin to Form Nitroglycerin (NG)

A round-bottom flask was charged with a magnetic stir bar and 20 mL of sulfuric acid, and then chilled in an ice bath. Ammonium nitrate (13.04 g (162.9 mmol)) was added at a rate such that the temperature of the nitrating solution did not exceed 15° C. Glycerin (2 mL (27.15 mmol), 100% purity, purchased from Sigma-Aldrich Co.) was added at a rate such that the temperature of the reaction mixture did not exceed 15° C. Once all the glycerin was added and the temperature of the reaction mixture began to decrease, the ice bath was removed and the reaction mixture was stirred for 3 hours at ambient conditions. The reaction mixture was added in one portion to 100 g crushed ice and stirred gently until all the ice melted. The resulting emulsion was transferred to a separatory funnel and extracted four times with 25 mL methylene chloride. The combined organic extracts were dried with $MgSO_4$ and then concentrated to produce NG as a clear pale yellow liquid (5.93 g of NG, a 96% yield). The reaction is shown below:

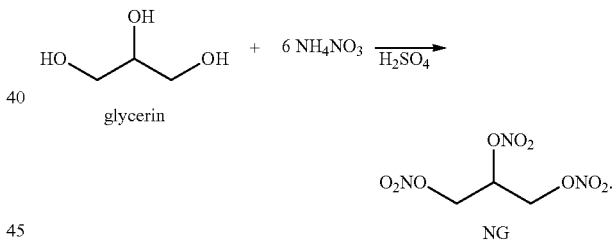

Figure 6:
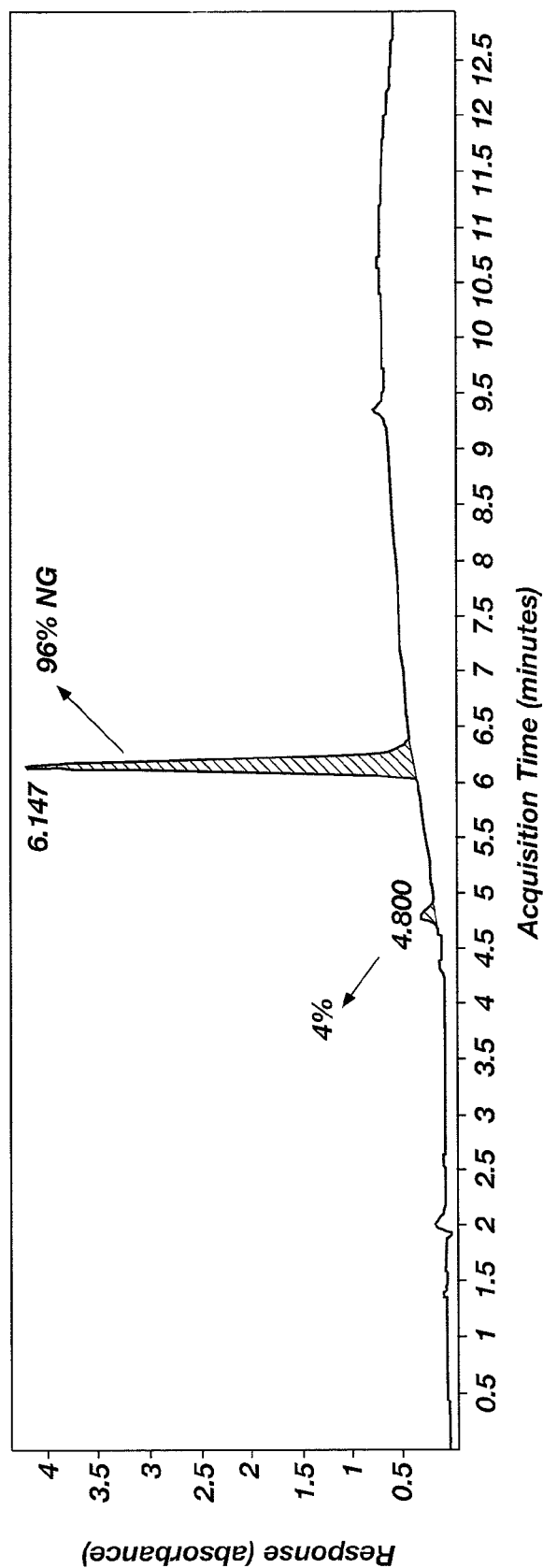

The NG was characterized by $^1H$ and $^{13}C$ NMR spectroscopy and HPLC. As shown in FIG. 6, the NG was about 96% pure. The $^1H$ and $^{13}C$ NMR spectra (not shown) confirmed the synthesis of NG.

While the invention is susceptible to various modifications and alternative forms, specific embodiments have been shown by way of example in the drawings and have been described in detail herein. However, the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method of producing a nitrate ester, comprising:
   combining sulfuric acid with at least one of ammonium nitrate and a metal nitrate to form a nitrating solution; and
   adding a polyol comprising at least one of triethylene glycol, pentaerythritol, diglycerol, 1,1,1-tris(hydroxymethyl)-ethane, 1,2,4-butanetriol, glycerin, diethylene glycol, and cellulose to the nitrating solution.

2. The method of claim 1, wherein combining sulfuric acid with at least one of ammonium nitrate and a metal nitrate to form a nitrating solution comprises combining from about 50% by weight to about 98% by weight of sulfuric acid with the at least one of ammonium nitrate and a metal nitrate.

3. The method of claim 1, wherein combining sulfuric acid with at least one of ammonium nitrate and a metal nitrate to form a nitrating solution comprises combining the sulfuric acid with at least one of sodium nitrate, potassium nitrate, ammonium nitrate, calcium nitrate, and magnesium nitrate.

4. The method of claim 1, wherein combining sulfuric acid with at least one of ammonium nitrate and a metal nitrate to form a nitrating solution comprises adding the at least one of ammonium nitrate and a metal nitrate into the sulfuric acid at a temperature of less than about 20° C.

5. The method of claim 1, wherein adding a polyol to the nitrating solution comprises adding the polyol to the nitrating solution comprising from about one molar equivalent to about two molar equivalents of at least one nitrate salt for each hydroxyl group of the polyol.

6. The method of claim 1, wherein adding a polyol to the nitrating solution comprises adding the polyol to the nitrating solution at a temperature within a range of from about 0° C. to about 80° C.

7. The method of claim 1, wherein adding a polyol to the nitrating solution comprises reacting nitronium ions in the nitrating solution with oxygen atoms of the polyol.

8. A method of producing a nitrate ester, comprising reacting an aliphatic polyol having at least three —OH functional groups with a nitrating solution comprising sulfuric acid and at least one of ammonium nitrate and a metal nitrate.

9. The method of claim 8, wherein reacting an aliphatic polyol having at least three —OH functional groups with a nitrating solution comprising sulfuric acid and at least one of ammonium nitrate and a metal nitrate comprises reacting the aliphatic polyol, the sulfuric acid, the at least one of ammonium nitrate and a metal nitrate, and water.

10. The method of claim 8, wherein reacting an aliphatic polyol having at least three —OH functional groups with a nitrating solution comprising sulfuric acid and at least one of ammonium nitrate and a metal nitrate comprises producing a nitrate ester.

11. The method of claim 10, wherein reacting an aliphatic polyol having at least three —OH functional groups with a nitrating solution comprising sulfuric acid and at least one of ammonium nitrate and a metal nitrate comprises reacting an aliphatic polyol having at least three —OH functional groups with a nitrating solution comprising from about one molar equivalent to about two molar equivalents of the at least one of ammonium nitrate and a metal nitrate for each nitrate group of the nitrate ester.

12. The method of claim 8, wherein reacting an aliphatic polyol having at least three —OH functional groups with a nitrating solution comprising sulfuric acid and at least one of ammonium nitrate and a metal nitrate comprises producing a nitrate ester comprising pentaerythritol tetranitrate, diglycerol tetranitrate, 1,1,1-tris(methylol)ethane trinitrate, 1,2,4-butanetriol trinitrate, or nitroglycerin.

13. The method of claim 8, wherein reacting an aliphatic polyol having at least three —OH functional groups with a nitrating solution comprising sulfuric acid and at least one of ammonium nitrate and a metal nitrate comprises adding the at least one of ammonium nitrate and a metal nitrate to the sulfuric acid at a temperature in a range of less than about 20° C.

14. The method of claim 8, wherein reacting an aliphatic polyol having at least three —OH functional groups with a nitrating solution comprising sulfuric acid and at least one of ammonium nitrate and a metal nitrate comprises adding the aliphatic polyol to the nitrating solution at a temperature of less than about 80° C.

15. The method of claim 8, wherein reacting an aliphatic polyol having at least three —OH functional groups with a nitrating solution comprising sulfuric acid and at least one of ammonium nitrate and a metal nitrate comprises:
adding the at least one of ammonium nitrate and a metal nitrate to the sulfuric acid at a temperature in a range of from about 0° C. to about 20° C.; and
combining the aliphatic polyol with the nitrating solution at a temperature in a range of from about 0° C. to about 80° C. to form a reaction mixture.

16. The method of claim 15, further comprising separating a nitrate ester from the reaction mixture.

17. The method of claim 16, further comprising purifying the nitrate ester.

18. A method of producing a nitrate ester, comprising:
reacting a polyol with a nitrating solution, wherein the polyol comprises at least one of triethylene glycol, pentaerythritol, diglycerol, 1,1,1-tris(hydroxymethyl)-ethane, 1,2,4-butanetriol, and glycerin, and wherein the nitrating solution comprises sulfuric acid and at least one of ammonium nitrate and a metal nitrate.

19. The method of claim 1, wherein adding the polyol to the nitrating solution comprises stirring the polyol with the nitrating solution.

20. The method of claim 8, wherein reacting an aliphatic polyol having at least three —OH functional groups with a nitrating solution comprising sulfuric acid and at least one of ammonium nitrate and a metal nitrate comprises reacting at least one of pentaerythritol, diglycerol, 1,1,1-tris(hydroxymethyl)-ethane, 1,2,4-butanetriol, and glycerin with the nitrating solution.

* * * * *

UNITED STATES PATENT AND TRADEMARK OFFICE
CERTIFICATE OF CORRECTION

PATENT NO. : 8,658,818 B2  Page 1 of 1
APPLICATION NO. : 12/953111
DATED : February 25, 2014
INVENTOR(S) : Nicholas A. Straessler, Alexander J. Paraskos and Michael P. Kramer It is certified that error appears in the above-identified patent and that said Letters Patent is hereby corrected as shown below:

In the specification:
COLUMN 1, LINE 22, change "(—$NO_2^+$)" to --(—$NO_2^+$),--
COLUMN 5, LINE 44, change "oxidized nitrogen species" to --oxides of nitrogen--

Signed and Sealed this
Twenty-second Day of September, 2015

Michelle K. Lee
*Director of the United States Patent and Trademark Office*